US010247705B2

(12) United States Patent
Pellegrino et al.

(10) Patent No.: US 10,247,705 B2
(45) Date of Patent: Apr. 2, 2019

(54) ASSET-CONDITION MONITORING SYSTEM

(71) Applicant: SENSOR NETWORKS, INC., Boalsburg, PA (US)

(72) Inventors: Bruce A. Pellegrino, Far Hills, NJ (US); James Barshinger, State College, PA (US)

(73) Assignee: SENSOR NETWORKS, INC., Boalsburg, PA (US)

( * ) Notice: Subject to any disclaimer, the term of this patent is extended or adjusted under 35 U.S.C. 154(b) by 565 days.

(21) Appl. No.: 14/839,694

(22) Filed: Aug. 28, 2015

(65) Prior Publication Data

US 2016/0109411 A1    Apr. 21, 2016

Related U.S. Application Data

(60) Provisional application No. 62/058,592, filed on Oct. 1, 2014, provisional application No. 62/137,532, filed on Mar. 24, 2015.

(51) Int. Cl.
*G01N 29/04* (2006.01)
*H04B 11/00* (2006.01)
(Continued)

(52) U.S. Cl.
CPC ....... *G01N 29/043* (2013.01); *G01N 29/0645* (2013.01); *G01N 29/11* (2013.01);
(Continued)

(58) Field of Classification Search
CPC ........... G01N 2291/0258; H04B 11/00; H04W 4/005; H04W 72/082; G01B 17/02; G01B 2210/58
See application file for complete search history.

(56) References Cited

U.S. PATENT DOCUMENTS 3,611,053 A    10/1971    Rowell
6,984,946 B2 *   1/2006    Donnelly ................ B60L 3/102
                                                                      105/61

(Continued)

OTHER PUBLICATIONS

International Search Report dated Dec. 18, 2015 for correlating PCT Application No. PCT/US2015/053448.

*Primary Examiner* — Elias Desta
(74) *Attorney, Agent, or Firm* — FisherBroyles LLP

(57) ABSTRACT

An ultrasound sensing system for monitoring the condition or integrity of a structure, comprising (a) a plurality of ultrasound sensors, each sensor being configured to receive at least one first electrical signal, transmit an ultrasound signal in response to the first electrical signal, receive at least one reflected ultrasound signal, and transmit a second electrical signal in response to the reflected ultrasound signal, the first and second electrical signals being analog; (b) at least one digital sensor interface (DSI) to which at least a portion of the sensors are connectable, the DSI being configured to transmit the first electrical signal and receive the second electrical signal, and to generate an A-scan signal based on the first and second electrical signals for each sensor, the DSI having circuitry for transmitting a digital signal based directly or indirectly on at least the A-scan signal, the digital signal including an address corresponding to the at least one DSI; (c) a digital bus configured to receive the digital signal from the at least one DSI; (d) a user interface connected to the bus to receive the digital signal; and wherein, in one embodiment, the sensors are mounted semi-permanently on the structure and the DSI is also mounted semi-permanently on or adjacent to the structure being monitored.

29 Claims, 7 Drawing Sheets

(51) Int. Cl.
*G01N 29/44* (2006.01)
*H04W 4/70* (2018.01)
*G01N 29/11* (2006.01)
*G01N 29/06* (2006.01)

(52) U.S. Cl.
CPC ............ *G01N 29/44* (2013.01); *H04B 11/00* (2013.01); *H04W 4/70* (2018.02); *G01N 2291/015* (2013.01); *G01N 2291/0234* (2013.01); *G01N 2291/0258* (2013.01); *G01N 2291/02854* (2013.01); *G01N 2291/044* (2013.01); *G01N 2291/106* (2013.01)

(56) References Cited

U.S. PATENT DOCUMENTS

| | | |
|---|---|---|
| 7,302,866 B1 | 12/2007 | Malkin et al. |
| 2005/0232079 A1 | 10/2005 | McDonald |
| 2007/0095160 A1 | 5/2007 | Georgeson et al. |
| 2009/0157358 A1 | 6/2009 | Kim |
| 2010/0206080 A1 | 8/2010 | Ruzzene et al. |
| 2012/0016607 A1* | 1/2012 | Cottrell ............ G05B 23/0229 702/62 |
| 2013/0185593 A1 | 7/2013 | Taylor et al. |
| 2013/0211548 A1 | 8/2013 | Leinen et al. |
| 2014/0039754 A1* | 2/2014 | Nishizawa ............ G07C 5/00 701/34.4 |
| 2014/0238136 A1 | 8/2014 | Ten Grotenhuis et al. |

* cited by examiner

ASSET-CONDITION MONITORING SYSTEM

CROSS REFERENCE TO RELATED APPLICATIONS

This application claims the benefit of U.S. Provisional Application No. 62/058,592, filed Oct. 1, 2014, and U.S. Provisional Application No. 62/137,532, filed Mar. 24, 2015, the entire disclosures of which are incorporated herein by reference.

FIELD OF INVENTION

The invention relates generally to a system for ultrasonically monitoring the condition and integrity of pipes and/or other structures or assets, such as those used in the oil and gas and power generation industries.

BACKGROUND

Wall thickness and the presence of defects such as cracks are important factors in determining the fitness-for-service of structures such as above and below ground pipes and tanks. When a pipe is in operation, it can be subject to corrosion and/or erosion due to the content, flow and/or environmental conditions inside or outside of the pipe. Cracks can form and propagate due to the presence of manufacturing defects, creep, thermal cycling, fatigue and environmental conditions resulting in high temperature hydrogen attack (HTHA) stress corrosion cracking, etc. Corrosion and/or erosion results in the reduction in wall thickness, which can reach a point at which operating conditions becomes unsafe, considering that the pipe can be pressurized and may contain hazardous or flammable materials. Likewise formation and propagation of cracks can cause similar unsafe conditions. A failure may cause catastrophic consequences such as loss of life and environmental damage in addition to the loss of the use of the asset, and any corresponding costs associated with repair, loss of capacity and revenue loss.

Ultrasonic non-destructive evaluation techniques are commonly used for evaluating the integrity of industrial components. In the case of measuring wall thickness reduction due to erosion/corrosion, the traditional process involves using a portable handheld instrument and ultrasonic transducer (probe) to measure the wall thickness. The instrument excites the probe via an electrical pulse, and the probe, in turn, generates an ultrasonic pulse which is transmitted through the structure. The probe also receives an echo of the ultrasonic pulse from the structure, and converts the pulse back into an electrical signal. The ultrasonic pulses that are transmitted into and received from a structure are used to determine the relative position of the surfaces (i.e. thickness) of the structure wall. More specifically, by knowing the travel time of the ultrasonic pulse from the outer wall to the inner wall and back ($\Delta T$) and acoustic velocity (V) of the ultrasonic pulse through the material of the structure (through calibration or just initialization), a wall thickness (d) can be calculated—i.e. $d = \Delta T * V / 2$. In a similar fashion, ultrasound can be used to detect the presence of defects such as cracks in bulk material or in welds. Here, the gauge is set up to look for the presence of ultrasonic echoes returning from the defect. The presence of an echo in a particular area of interest would indicate the presence of a flaw. There are many variants of these two basic descriptions of ultrasonic thickness gauging and flaw detection that are known to skilled practitioners of ultrasonic nondestructive evaluation.

These approaches require an operator to manually position a probe on the wall of the asset to take a reading. Not only does this necessitate the operator manually taking each reading, but also the measurement location must be accessible, which can be challenging and costly. For example buried pipelines require excavation to access, insulated pipe requires costly removal of the insulation, offshore assets require helicopter or boat access, and elevated vessels may require scaffolding or crane access. While the measurement is relatively simple, the cost of access (scaffolding, excavation, insulation removal, etc) is often much higher than the cost of measurement. Moreover, the operator may be subjected to hazardous conditions while taking the readings.

Another problem with the traditional approach is that the data is captured on a proprietary device, making the distribution and further processing of the data inconvenient and potentially subject to translation errors if the data is recorded manually. That is, once the data is acquired by the handheld device, the device usually needs to be connected to a computer running a proprietary software to download, analyze and report the data. Often times the software is only licensed to a single computer so multiple software licenses are required. Furthermore, the technology requirements for the software installations can be challenging and maintenance can be problematic—e.g., computer replacement, operating system upgrades, etc. Additionally, inspection reports are then written and often shared with the operator or asset owner via emailed or paper reports, but not via cloud based data access.

Furthermore, to obtain trending data with thickness resolution of 0.001" or better requires that the transducer be placed in the same exact location for consistent readings at regular time intervals. This is difficult and often impractical especially when the data-capture rate needs to be frequent. Variations in operator and/or equipment tend to skew the quality and integrity of the measurement data.

One approach for avoiding some of the aforementioned problems is to use installed sensors/systems for asset-condition or -integrity measurement. The sensors are permanently or semi-permanently installed on the asset and can be covered with soil, insulation and/or can be wired to a convenient place for easy user access. This also overcomes the limitation in manual thickness measuring that it is never possible to place the sensor in the same position for subsequent readings resulting in inherent measurement error Automated systems require no operator to be in the vicinity of the asset and can stream data to a control room or to an operator's desk.

Current permanently- or semi-permanently installed systems tend to suffer, however, from a number of shortcomings. For example, some of the systems require point-to-point connections between the user interface and the sensors. This becomes problematic as the number of sensors on a structure increases, requiring bundles of wire to be run to the interface. Additionally, conventional systems tend to require proprietary user interfaces to receive signals from the sensors and to apply proprietary algorithms to convert these signals to usable data. Thus, the user is forced to interface or download information from these proprietary controllers to a PC/tablet or other user device. Still other conventional systems use wireless signals between the sensor and the controller. Again, these links tend to be proprietary and require a proprietary controller to receive and process the data from the sensors. Such systems are also inappropriate for underground use. Further, wireless transmissions tend to be slower and thus latency in the system can be an issue. Yet another problem of the conventional system is analog signals between the sensors and the controller. As is known, analogs signals are more susceptible to corruption and degradation, and thus misinterpretation, especially as the distance between the sensor and the controller increases.

Therefore, Applicants recognize a need for a system that is modular and facilitates non-proprietary transmission of digital signals using off-the-shelf user interfaces. The present invention fulfills this need among others.

SUMMARY OF INVENTION

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

Applicants recognize that the proprietary, analog user interface used in conventional ultrasonic wall thickness measuring systems is cumbersome and inconvenient, and subject to corruption/attenuation and other undesirable effects. To minimize these shortcomings, Applicants recognize that "pushing" the proprietary and analog circuitry as close to the sensors as practical and using a digital bus to interconnect the sensors increases the integrity of the data obtained and imparts modularity by enabling the use of conventional, off-the-shelf user interfaces. In particular, Applicants propose a system comprising a digital bus interconnecting one or more digital sensor interfaces (DSIs), which are proximate to the analog sensors and contain the necessary circuitry to convert the analog sensor signals to digital signals and transmit these digital signals on the digital bus. By locating the proprietary interface—i.e., the DSI—as close to the sensors as practical, most of the cabling and signal transmission is digital and non-proprietary, and thus can be readily integrated with off-the-shelf consumer electronic devices such as tablets, smart phones, and laptops without the need for converting/downloading or otherwise manipulating signals.

Such a system provides for a number of important benefits. For example, in one embodiment, the system of the present invention uses a standard digital, multi-drop communication link, such as RS485/Modbus, or CANbus, to connect the user interface with the DSIs which in turn are connected to the sensors. The multi-drop bus allows a single multi-pair wire to access multiple sensor and sensor installations reducing cable cost and installation complexity. Furthermore, standard bus/protocol allows DSI and sensor installation to be easily connected to other plant equipment such as DCS (distributed control system) or SCADA (supervisory control and data acquisition) system.

In one embodiment, the user interface (i.e. tablet or cell phone) comprises digital connectivity via wired means such as USB or wireless means such as Wi-Fi or Cellular communications. This enables the data to be pushed from the user interface via wired or wireless connections. Such connectivity facilitates cloud data storage which may be used as a collection point for the ultrasonic wall thickness data as well as related information about the installation. Examples of related information could be device information such as serial numbers, asset information, GPS coordinates, installation photographs, nominal wall thickness information, wall thickness limits, and 3D asset models. The ability to push data to the cloud also facilitates hosting the system through the Web. A Web-hosted user interface may be used for data display and analysis such that an asset operator can view and analyze its data from any Web connected computer or handheld device. Cloud storage access also provides enhanced visibility to data and can also be advantageous for meeting archiving and reporting requirements. It can further offer the ability to trigger automated alarms when an alarm threshold condition is met. Such alarms could be delivered via email or text message for instance. An additional advantage of cloud storage/computing is the potential for advanced data post processing and analytics.

Additionally, because the DSI is near the sensors and thus can perform computations on the analog sensor signals before they become distorted, the DSI may be configured to execute relatively complex signal processing to provide for a host of different outputs and monitoring options, including, for example, ultrasonic imaging techniques such as ultrasonic phased array/delay and sum beam forming and full matrix capture (FMC)/total focusing method [TFM].

The proposed DSI is a general purpose ultrasonic interface to a variety of sensor types. Advantageously, the electrical design of the DSI allows the connection of the transmitter and receiver channels to separate transmit and receive elements. These elements can be separate transducers or can be individual elements within a single transducer housing as may be present in a dual element transducer or in an array type of transducer. Dual element transducers are particularly suited to thickness measurement of corroded and/or rough surfaces. Array transducers are useable for electronic control of the beam and can be used with the FMC and TFM methods mentioned previously.

Accordingly, one aspect of the present invention is an ultrasonic system incorporating a multi-drop digital bus having a standard protocol. In one embodiment, the system comprises: (a) a plurality of ultrasound sensors, each sensor being configured to receive a first electrical signal, transmit an ultrasound signal in response to the first electrical signal, receive a reflected ultrasound signal, and transmit a second electrical signal in response to the reflected ultrasound signal, the first and second electrical signals being analog; (b) at least one digital sensor interface (DSI) to which at least a portion of the sensors are connectable, the DSI being configured to transmit the first electrical signal and receive the second electrical signal, and to generate an A-scan signal based on the first and second electrical signals for each sensor, the DSI having circuitry and software for transmitting a digital signal based directly or indirectly on at least the A-scan signal, the digital signal including an address corresponding to the at least one DSI; (c) a digital bus configured to receive the digital signal from the at least one DSI; and (d) a user interface connected to the bus to receive the digital signal.

Another aspect of the invention is a DSI proximate the sensors for use in an ultrasound sensing system for monitoring the condition or integrity of a structure. In one embodiment, the DSI comprising: (a) analog transmit and receive circuitry to which at least one or more sensors are operatively connectable, the analog transmit and receive circuitry being configured to transmit a first electrical signal to each of the sensors and to receive a second electrical signal from the each of the sensors responsive to the first electrical signal; (b) an analog to digital converter to convert data related to the first and second signals to a digital signal; (c) a digital processor to calculate an A-scan signal based on the digital signal; and (d) a digital transceiver to transmit digitally an output signal based on the A-scan signal.

DETAILED DESCRIPTION

Figure 1:
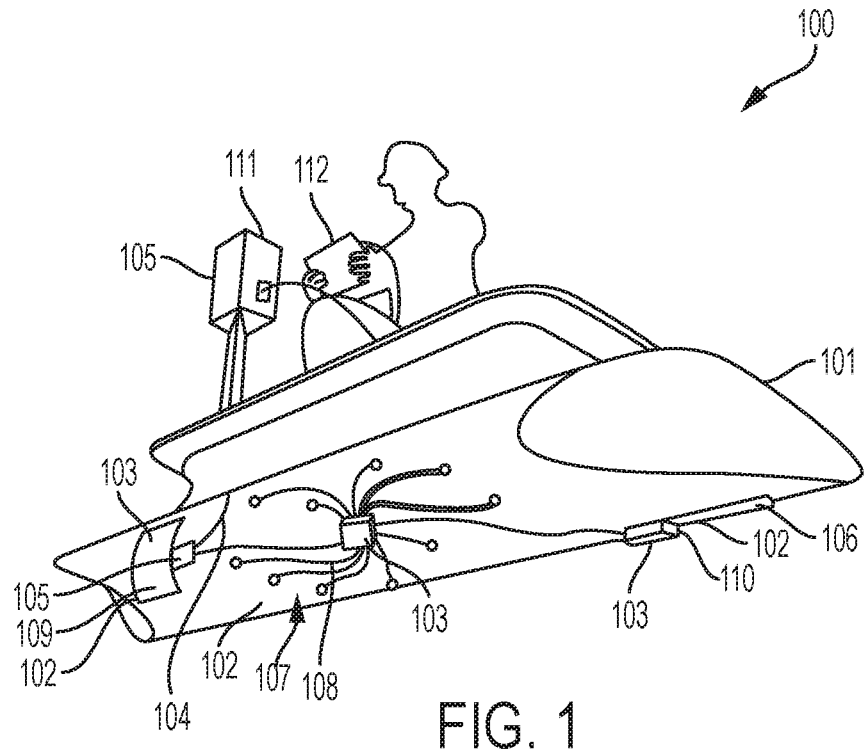
FIG. 1 shows a perspective view of one embodiment of the ultrasonic wall thickness measurement system of the present invention.
Figure 2:
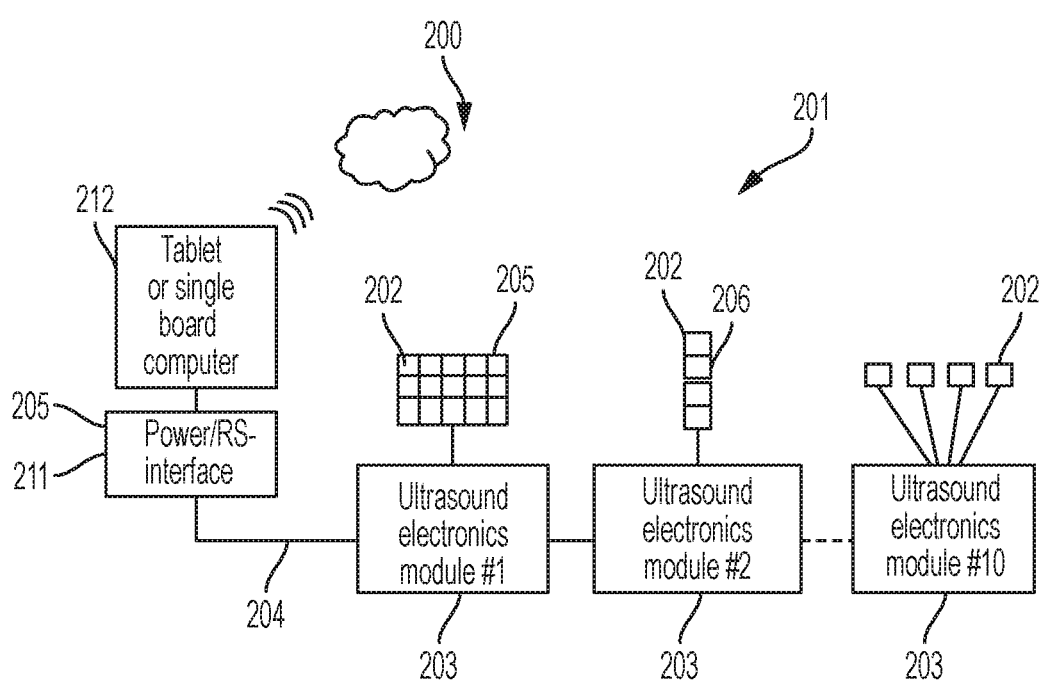
FIG. 2 shows a schematic of the embodiment shown in FIG. 1.

Referring to FIGS. 1 and 2, a perspective view and schematic view of one embodiment of the ultrasound sensing system 100, 200, respectively, of the present invention is shown. In this embodiment, the system 100, 200 functions to determine wall thickness of a structure 101, and comprises a plurality of ultrasound sensors 102, 202. Each sensor 102, 202 is configured to receive a first electrical signal, transmit an ultrasound signal in response to said first electrical signal, receive a reflected ultrasound signal, and transmit a second electrical signal in response to said reflected ultrasound signal. The first and second electrical signals are analog. The system 100, 200 also comprises at least one digital sensor interface (DSI) 103, 203 to which at least a portion of said sensors 102, 202 are connectable. The DSI is configured to transmit said first electrical signal and receive said second electrical signal, and to generate a time-voltage waveform commonly known as an A-scan based on said first and second electrical signals for each sensor. The DSI has circuitry for transmitting a digital signal based directly or indirectly on at least said A-scan signal. In one embodiment, the digital signal includes an address corresponding to said at least one DSI. The system 100, 200 also comprises a digital bus 104, 204 configured to receive said digital signal from the DSI(s), and a user interface 105, 205 connected to said bus to receive said digital signal. These components are described in greater detail below.

DSI

At the heart of the system 100, is the DSI 103, 203. The DSI functions to interface with the sensors 102, 202 and generate a digital signal related to the physical characteristics of a particular structure 101, 201, including, for example, wall thickness, anomalies/cracks, or even an ultrasonic image. In one embodiment, the DSI interfaces with the sensors by transmitting and receiving the first and second electrical analog signals, as described above, and generating an A-scan signal from which the wall thickness of the structure can be derived. A-scan signals are well known and relate generally to a data presentation by which intelligence signals from an object location are displayed. As generally applied to pulse-echo ultrasonics, the horizontal and vertical sweeps are proportional to time or distance and amplitude or magnitude respectively. Thus the location and magnitude of acoustical interface are indicated as to depth below the sensor. It should be understood, however, that the A-scan signal may be presented in different forms after processing within the DSI.

Additionally, the DSI functions to generate a digital signal for output onto the digital bus 104, 204 that is based on the A-scan signal. An important aspect of the invention is that the DSI generates and transmits the digital signal which is based on known, non-proprietary protocols allowing it to be transmitted on known, non-proprietary digital buses as described below. The digital signal may be based directly or indirectly on the A-scan signal. More specially, in one embodiment, the A-scan signal is merely converted to a digital signal, which is then transmitted on the digital bus (described below in greater detail). Alternatively, the digital signal may be indirectly based on the A-scan scan. That is, the A-scan signal may be converted to thickness data as described above, and then the thickness data may be transmitted as a digital signal over the bus. Whether the signal is directly related to the A-scan signal or indirectly related to the A-scan signal is not critical to the claimed invention provided that the output of the DSI is a digital signal comporting with known protocols.

As discussed below, a significant benefit of converting the analog signal in close proximity to the sensors, and transmitting a responsive digital signal along a digital bus is that the digital signal tends to be less susceptible to distortion/degradation than an analog signal. This allows for a number of desirable features, including, for example, longer distances between the DSI and the user interface and multiple DSI drops. Additionally, because the DSI is near the sensors and thus can perform computations on the analog sensor signals before they become distorted, the DSI may be configured to execute relatively complex signal processing to provide for a host of different outputs and monitoring options, including, for example, ultrasonic imaging techniques such as ultrasonic phased array/delay and sum beam forming and full matrix capture (FMC)/total focusing method [TFM] which are discussed in greater detail below.

In one embodiment, the DSI can be configured to store data related to the inspection, including the ultrasonic parameters, such as instrumentation gain, gate positions, and calibration data, as well as contextual data such as GPS coordinates for the DSI and TMLs, asset information, tag numbers, etc. This data may accompany or be integrated with the digital signal transmitted on the digital bus by the DSI, thereby providing the user with critical information related to the specific DSIs, sensors and contextual information of the readings without user intervention.

In one embodiment, the DSI stores parameters related to the asset and other system information. For example, stored DSI parameters may include the following: Company ID Number; Company Name; Company Address; Phone Number; Site/Division; Plant; Asset; Collection Point ID; Collection Point Description; Collection Point GPS Coordinate; Modbus Address; DSI Serial Number; DSI Tag Number; DSI Firmware Version (Micro). DSI Firmware Version (FPGA); DSI GPS Coordinate; # of DSIs in chain; # of Probes Attached; Result Packet Version; Baud Rate; and Parity & # of Stop Bits.

Additionally, the DSI may be configured to store data related to sensor parameters. (As discussed below, the sensors are not generally intelligent devices and thus usually do not have the ability to store parameters.) Data corresponding to these parameters Examples of sensor parameters stored in the DSI may include the following: Probe Model; Probe Type; Probe Location; Probe GPS Coordinates; Nominal Material Thickness; Minimum Material Thickness; Material Velocity; and Number of Valid Setups. Parameters such as minimum material thickness can be used to automatically determine alarm states once a measurement has been performed. Other parameters related to automated alarming are contemplated to be stored in the DSI memory. The present invention also contemplates storing images of the sensors and/or their locations on the asset to provide the user with a visual indication of where on the asset the sensor data pertains.

Additional parameters associated with the measurement may include the following: DSI Temperature; Material Temperature; Status; Calculated Thickness; Data/Time Stamp; Last Measure Thickness; LMT Date/Time Stamp; Pulser Width; Gain; Mux Switch Settings/# of Averages; Ascan Start Position; Gate 1 Start Position; Gate 1 Width; Gate 1 Threshold; Gate 1 Mode; Gate 1 TOF; Gate 1 Amplitude; Gate 2 Start Position; Gate 2 Width; Gate 2 Threshold; Gate 2 Mode; Gate 2 TOF; Gate 2 Amplitude; Gate 3 Start Position; Gate 3 Width; Gate 3 Threshold; Gate 3 Mode; Gate 3 TOF; and Gate 3 Amplitude.

This data may be collected in different ways. For example, some of the data such as sensor data and DSI related data may be self-generated by the DSI during its initialization. Alternatively, this data may be entered by the user or otherwise downloaded by the user. Data related to the context of a particular reading may be obtained by the DSI at the time of the reading. Still other techniques for obtaining and storing data related to these parameters will be known to one of skill in the art in light of this disclosure.

Once theses parameters are stored, the results reported by the DSI are essentially standardized. Specifically, in one embodiment, the user is not required to enter data regarding the particular sensors being used or the context of the reading. That information is provided automatically with the reading data according to the user's preference. The information ensures a uniform inspection without regard to operator knowledge of the installation. Thus, the inspection results are consistent and data integrity is ensured.

The DSI may also use self-diagnostic information to indicate the "health" and proper operation of the DSI. Although different approaches for self-diagnoses are contemplated in this disclosure, one approach involves the DSI performing a self-check when powered up and/or when prompted to acquire data from the sensors. Such self-checks are well known to those of skill in the art in light of this disclosure. Once the diagnostic information is obtained, it can be compared to stored parameters corresponding to a healthy system to determine if a problem exists. In one embodiment, if a problem with the DSI or associated sensor is detected by the DSI, a message is transmitted on the digital bus indicating the problem, at which point the DSI may await instructions or take itself or a sensor off-line if the problem is severe enough.

The DSI may be configured to interface with any known sensor. For example, in one embodiment, the DSI is a dual-channel ultrasonic device, meaning that it has two independent, analog, transmit and receive channels. These channels can be used independently, each with an ultrasonic sensor individually or together with a dual element ultrasonic sensor. In one embodiment, the DSI acts as a single-channel ultrasonic device, meaning that it can be configured to transmit and receive on any channel. These channels can be used independently, each channel being connected to a single ultrasonic sensor, or multiple channels being connected to a multi-element ultrasonic sensor, such as an array.

In one embodiment, each ultrasonic channel is multiplexed using an array of switches to increase the number of measurement points. For example, if each channel of the DSI is multiplexed to 16 outputs, then each channel can be connected to 16 ultrasonic sensors for a total of 16 measurement points. Alternatively, the channels may be used in pairs with dual-element sensors for a total of 8 measurement points.

Figure 4:
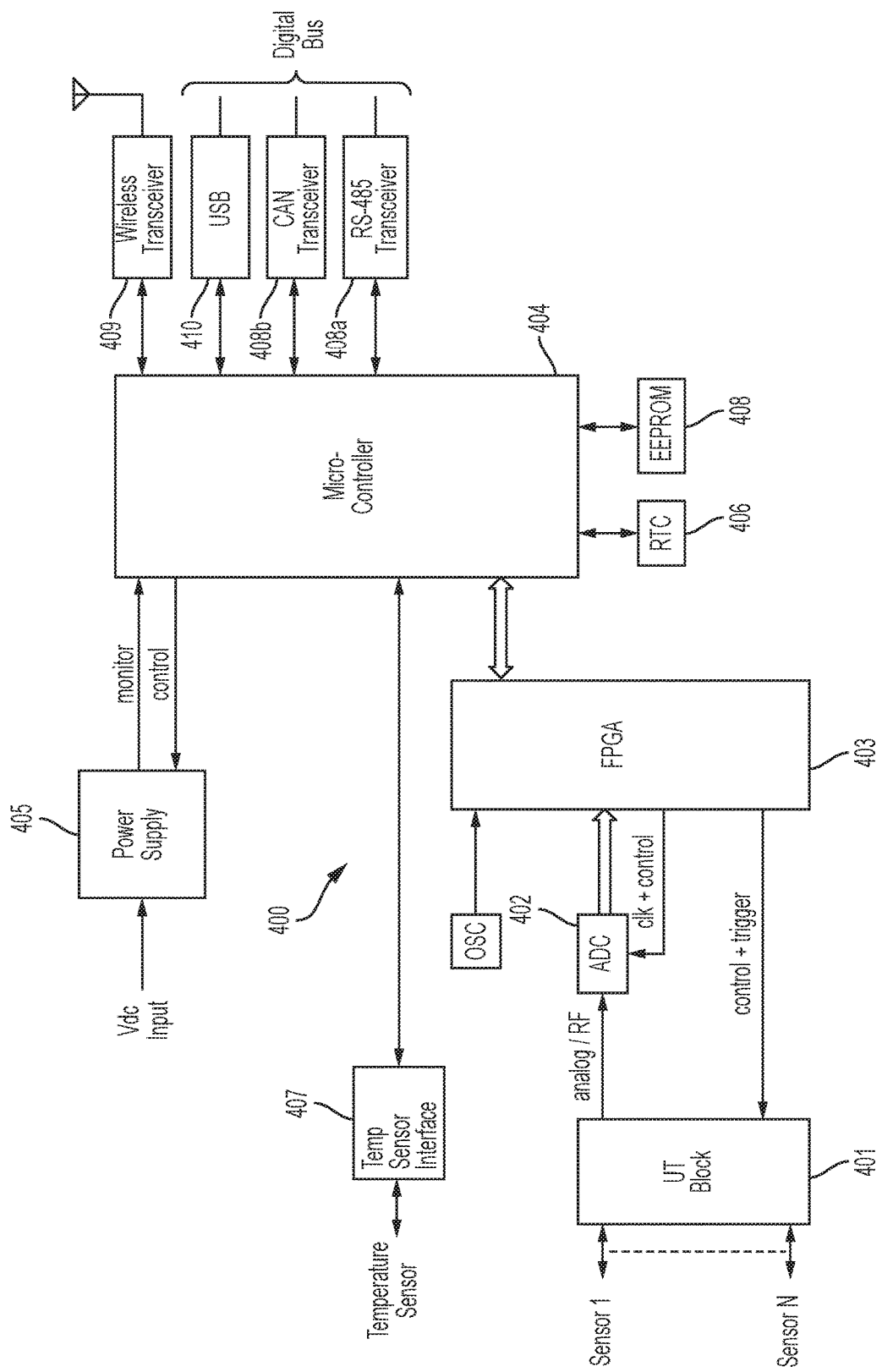
FIG. 4 shows a block diagram of one embodiment of a DSI unit of the system of present invention.

Referring to FIG. 4, a block diagram of the architecture 400 of a specific embodiment of the DSI is considered in detail. The analog part of the electronics (transmitter/receiver and multiplexers are not shown in any detail and are simply shown as the UT Block 401. From the UT block 401, the analog RF signal is converted to digital data by the analog to digital converter (ADC 402), preprocessed in a field programmable gate array (FPGA 403) and fed into the microcontroller 404. Around the microcontroller are various peripheral components including the power supply 405, Real Time Clock 406, temperature sensor interface 407, serial EEPROM memory 408, and communication ports 408, such as, RS485 and CAN transceivers 408*a*, 408*b*, respectively, for the multi-drop network, a wireless transceiver 409 and a USB port 410.

Figure 11:
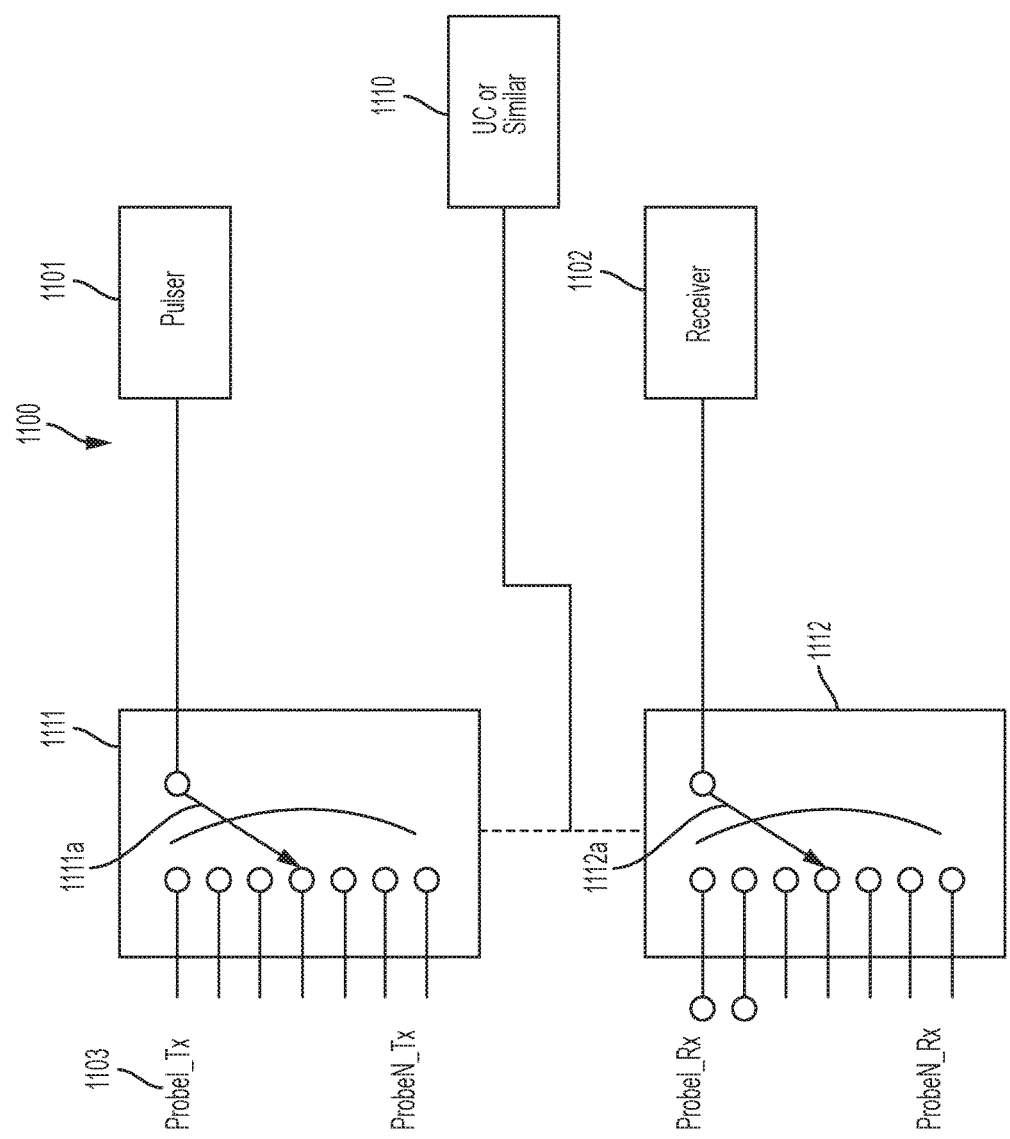
FIG. 11 shows a schematic of one embodiment of the dual probe multiplex.

Referring to FIG. 11, one embodiment of the dual probe multiplexer 1100 is shown. In this embodiment, dual element transducers are supported by the multiplexer or circuit 1100. As shown, the circuit is configured to allow a pulser 1101 and receiver 1102 to be connected to separately to individual transmit 1111 and receive elements 1112 of sensors 1103. A common control 1110 (microcontroller or similar) is used to ensure the settings of each individual switch 1111*a*, 1112*a* are set such that the TX and RX elements in the probe are connected to the pulser and receiver channels at the same time. One of the key elements is the use of separate switches for TX and RX channels. This separation allows for maximum electrical isolation between the TX and RX sides of the probe, thus reducing electrical crosstalk and thus maximizing measurement performance.

Sensors

The sensors function to convert between electronic signals and ultrasonic signals. (As used herein, the term "signal," unless otherwise indicated, may be electrical or ultrasonic, and may be in the form of electrical energy, sound pulse and other forms of electromagnetic or sound waves.) Such sensors are well known and are also referred to as transducers. Typically sensors comprise a piezoelectric material such as lead zirconate titanate (PZT).

Figure 5:
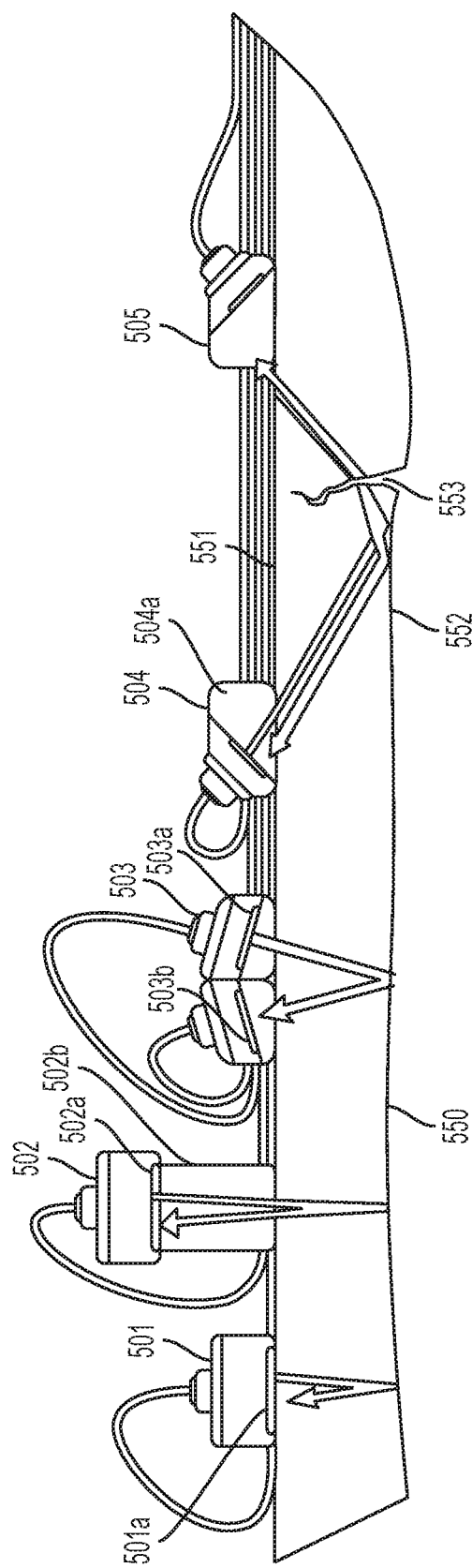
FIG. 5 shows different sensor configurations.

In one embodiment, the system of the present invention is configured to interface with most known or commercially-available ultrasonic sensor, thus avoiding the need for proprietary sensors and their inherent expense and limited availability. For example, referring to FIG. 5, a variety of sensors is shown for determining wall thickness and detecting cracks. The single-element sensor 501 both transmits and receives ultrasonic signals from the same element 501*a*. Such a sensor is relatively inexpensive and allows one sensor to operate on just one channel. In one embodiment, a single-element delay sensor 502 is combined with a solid (delay line) 502*b* such that the delay line is disposed between the sensor element 502*a* and the asset 550. The delay line functions to extend the travel time for an ultrasonic signal, thereby increasing the time between the transmit and receive function, which improves the near surface resolution and also measurement accuracy of single element sensors.

Another approach to improve measurement resolution is to use a dual-element sensor 503, which transmits an ultrasonic signal from one element 503a, and receives the reflected ultrasonic signal with a second element 503b. Although application needs may vary, generally a dual-element sensor can be advantageous for measuring heavily corroded surfaces as the electrical separation between transmit and receive channels allows for the use of increased signal amplification without the deleterious effect of amplifier saturation and recovery due to the transmission pulse.

To measure cracks, voids, welds, or other anomalies that are not parallel to the mounting surface 551 of the asset 550, but generally more perpendicular to the mounting surface, an angle-beam longitudinal wave sensor shear wave sensor 504 may be used. In one embodiment, the angle-beam sensor 504 is configured with an angled spacer (wedge) 504a to angle the sensor such that it refracts a signal into the asset that is angled relative to the rear surface 552 of the asset. When the signal impinges on the rear surface 552, it is reflected at the same angle (angle of refraction) and continues to propagate in the asset wall 550. As shown, if the signal encounters a crack 553 or similar anomaly, the signal is reflected such that it reflects off of the rear wall back to the sensor 504. Alternatively, an additional angle beam sensor 505 may be configured to receive the signal from the transmitting transducer. A defect in the path of the signal will block the transmission to the receiver, indicating its presence. The single, delayed, dual element, angle-beam L and shear wave sensors are well known in the art. Examples of commercially-available sensors are available from manufacturers such as Olympus NDT, Imasonic, and Blatek.

In one embodiment, groups of sensors are arranged in arrays such as a two dimensional array 105, 205 or a linear array 106, 206, and the arrays interfaced with DSIs as described below. In one embodiment, the array of sensors is fixed semi-permanently to the asset, thus facilitating a wall thickness measurement at the location of each sensor. The sensor array may be implemented in various embodiments. For example, referring to FIG. 1, a medusa configuration 107 is shown in which the sensors consist of individual probes and are cabled to the DSI via relatively short (<6 ft) cables 108. In another embodiment, the sensor array and DSI are implemented in the same physical package 109, 110 as shown in FIG. 1. In this embodiment, the array elements can be large and only operated individually or they can be small (<4 wavelengths) and be used in groups to electronically manipulate the ultrasonic beam, and is typically referred to as a phased array. An advantageous embodiment when using a phased array transducer using such processing methods as TFM allows the simultaneous inspection for both thickness and flaw detection. In another embodiment, the array sensor is fabricated such that it is flexible and can conform to the curved surface of a pipe, pipe elbow or vessel.

As mentioned above in connection with the DSI, each sensor's unique location, both relative to the other sensors in the array and their absolute location as installed on the industrial asset, can be permanently encoded, via a unique serial number or GPS location into the monitoring system for accurate tracking of all future measurements.

In another embodiment, provisions for temperature measurement are included in the system with associated sensors such as thermocouples and thermistors, and associated circuitry and software within the DSI. In one embodiment, there is at least one temperature measuring device per ultrasonic probe. For example, the temperature monitoring devices may be attached to or embedded into the ultrasonic transducers. In another embodiment, one temperature measuring device is used per several ultrasonic sensors. Temperature measurements are taken adjacent in time (just before, during, or after) an ultrasonic measurement and are used to adjust the ultrasonic measurement for changes in ultrasonic (acoustic) velocity due to temperature change. This is required to make more accurate (precise) ultrasonic thickness measurements for example. A software algorithm embedded in the thickness measurement ($d=v/2*T$) can automatically correct "v" for its predicated change in acoustic velocity as a function of asset temperature changes. Sensors for temperature measurement are well known and include, for example, resistance temperature detector (RTDs) or thermocouple Digital Bus The digital bus functions to interconnect the various DSIs on a common conduit with the user interface. Multiple DSIs may be connected to such a network in a linear, multi-drop configuration with a single conductor, such as coaxial cable. In one embodiment, the digital bus comprises a single cable that provides both power and digital communications to the DSIs. In an alternative configuration, the DSIs are interconnected by a four conductor cable, two conductors for communication and two for power. Still other configurations of the digital bus will be apparent to one of skill in the art in light of this application.

The digital bus uses a network protocol that supports multi-drop communications is used such that a single wire (or twisted-pair) can address multiple DSIs. The digital bus may use either parallel or bit serial connections, and can be wired in either a multi-drop (electrical parallel) or star topology or connected by switched hubs in the DSIs, as in the case of USB. Because the digital bus provides for multiple drops, one-to-one connections between the user interface and the sensors are eliminated. Rather, a single conduit, such as a coax, can interconnect the various DSIs and the user interface, thus simplifying installation and improving the integrity of the system.

The digital bus may be any known or later-developed digital bus facilitating multiple drops using standard protocols. In one embodiment, the digital bus is based on the TIA-485-A standard, also known as ANSI/TIA/EIA-485, TIA/EIA-485, EIA-485 or RS-485, which is a standard defining the electrical characteristics of drivers and receivers for use in balanced digital multipoint systems. The standard is published by the Telecommunications Industry Association/Electronic Industries Alliance (TIA/EIA), and is hereby incorporated by reference. In another embodiment, the digital bus is based on CAN Bus (controller area network), which is a message-based protocol, designed specifically for automotive applications but now also used in other areas such as aerospace, maritime, industrial automation and medical equipment. In yet other embodiments, the digital bus is Universal Serial Bus (USB), Ethernet, or Power over Ethernet (PoE). Still other digital buses will be obvious to one of skill in the art in light of this disclosure.

User Interface

The user interface 105, 205 functions as an interface between the system and a user and has a variety of different embodiments. Because the digital bus is preferably (but not necessarily) a standard bus, in one embodiment, the interface may comprise standard, off-the-shelf components for facilitating a connection to the DSIs.

For example, in one embodiment, the user interface 105 is simply a connector 111, 211 for interconnecting a user mobile computational device 112, 212 (e.g., a tablet, laptop computer, or smart phone) to the system. In this way, the connector of the user interface functions to provide a "tap" for the user to access the system. The access may be via a standard wired or wireless connection. In such an embodiment, the user's mobile device is used to connect periodically to the DSIs and to obtain data from the sensors.

Figure 6:
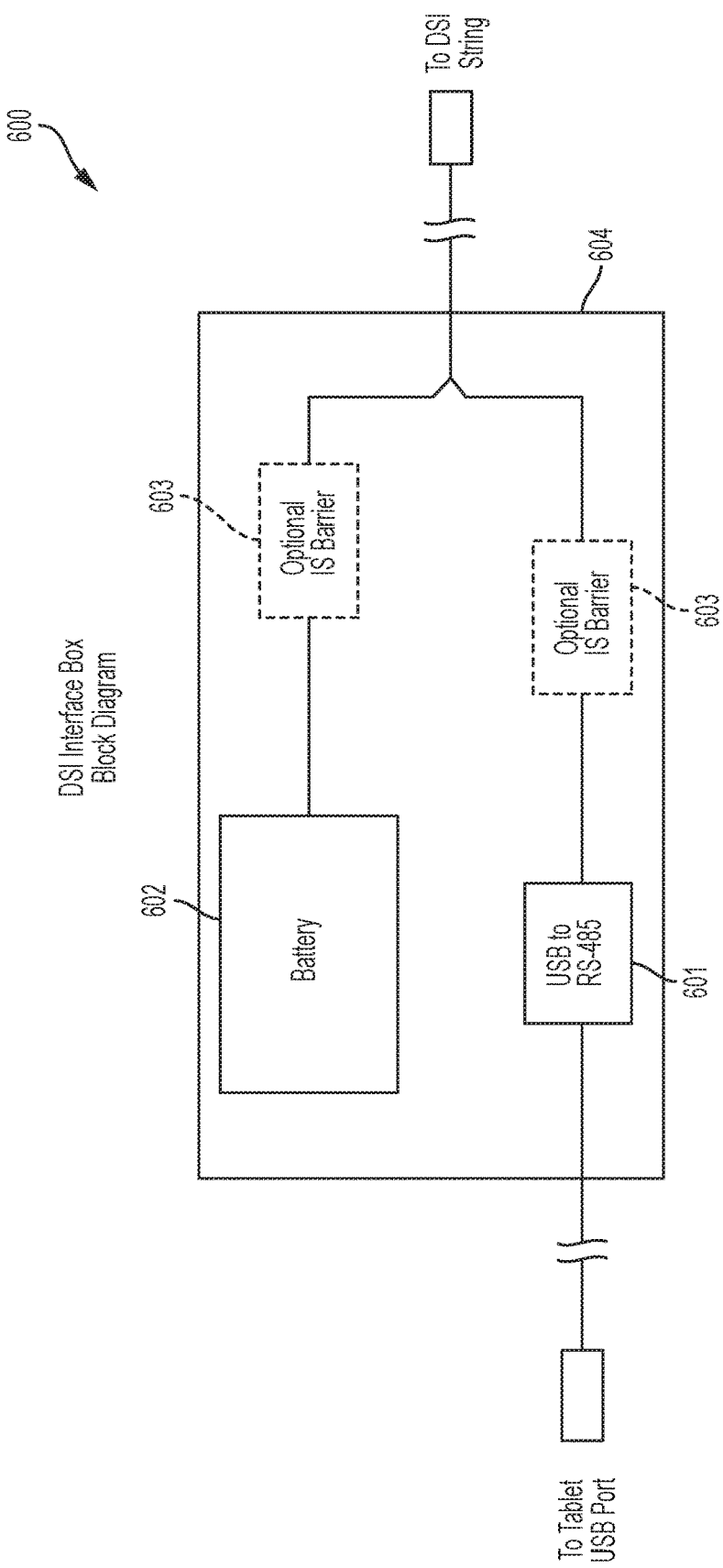
FIG. 6 shows a schematic of one embodiment of the interface box between the user hand-held device and the DSI.

In one embodiment, the user interface comprises an interface between the digital bus and the user's mobile device. It should be understood that embodiments of such a user interface may vary according to application and user needs. For example, referring to FIG. 6, in one embodiment, the interface 600 has one or more of the following features: (1) a converter 601 to convert the digital bus between formats—e.g. to convert between USB (common short distance PC bus format) to RS-485 (common long distance industrial bus format); (2) a battery 602 to power the DSIs (unless the user's mobile device (e.g., PC/tablet) has sufficient battery capacity to power the DSIs); (3) intrinsically safe (IS) barriers 603 for the both the digital bus and power outputs to limit energy to the DSIs if the DSIs are placed in a potentially explosive atmosphere; and (4) a housing 604 which may be NEMA rated according to the application. It should be understood that the interface 600 may also contain industry standard connectors for interfacing with the user's device and with the digital bus.

In another embodiment, the user interface comprises a permanently-installed controller 302 (see FIG. 3a) for communicating with the DSIs. The controller may be any know device adapted to interface with the DSIs on the digital bus and to withstand the environment in which the structure is situated. In one embodiment, the controller is a commercially available, non-proprietary computational device such as, a ruggedized tablet or laptop computer, or other portable computer. In one embodiment, the controller or mobile device is configured with software for providing a graphical user interface enabling the user to configure and operate the DSIs as well as to process, store and display data. In another embodiment, the controller is not a computational device, but rather is configured to transmit data to a computation system, e.g. a cloud-based system. In another embodiment, the controller is a computational device which also uploads data as described below.

It should be understood that the present invention contemplates various user interfaces and that other user interfaces not disclosed herein will be obvious to those of skill in the art in light of this disclosure.

Upload Connection

As mentioned above, the controller or mobile device may be configured to upload data from the DSIs. Accordingly, in one embodiment, the permanently-installed controller or mobile device is a "connected" device having a standard wired digital connection such as USB, or more preferably, a wireless connection such as Wi-Fi, telemetry, or cellular communications. The latter configuration allows the controller to collect the data and then push data to cloud storage for easy access by inspection personnel or asset owners. As used herein, the term cloud-based storage is a model of data storage where the digital data is stored in logical pools, the physical storage spans multiple servers (and often locations), and the physical environment is typically owned and managed by a hosting company. Cloud storage services may be accessed through a co-located cloud compute service, a web service application programming interface (API) or by applications that utilize the API, such as cloud desktop storage, a cloud storage gateway or Web-based content management systems. Thus, cloud-based storage for the ultrasonic measurements and related installation parameters enables the use of web-based data access from any fixed or mobile device having Internet connectivity. In one embodiment, access through web connected devices and a browser based interface bypasses the need for backend software that must be locally loaded and managed.

In one embodiment, the controller or mobile device transmits the A-scan signal or similar signal in essentially "raw" form for cloud-based computing. Cloud computing relies on sharing of resources to achieve economies of scale. Cloud computing focuses on maximizing the effectiveness of the shared resources. With cloud computing, multiple users can access a single server to retrieve and update their data without purchasing licenses for different applications. Thus, in this embodiment, cloud computing performs the calculations on the A-scan signal to determine wall thickness or detect flaws including cracking. The calculations can be relatively simple such as measuring wall thickness or complex such as the generation of images using full matrix capture and the total focusing method. Cloud computing enables this paradigm as the power and computational requirements that would otherwise be required on the DSI would result in excessive cost and system complexity.

Because of the system's modularity and non-proprietary user interface, the process for converting the A-scan signal to thickness data can be performed anywhere in the system (e.g., DSIs, controller, user device) or outside the system (e.g., in the Cloud). For example, the DSI can be configured to generate the thickness data from the A-scan signal, or, alternatively, the controller or mobile device can be configured to not only receive data from the DSI but also analyze and display the wall thickness data. Alternatively, the calculation may be performed by a computer outside of the system after the data is uploaded to the Cloud or other data store. Generally, determining when and where to calculate the thickness data from the A-scan signal is a question of optimization. For example, it may be preferable to convert the A-scan signal to thickness data in the DSI to save on storage space because the A-scan signal data consumes more space than the thickness data. On the other hand, converting this signal to thickness data tends to require more processing power, thus, more energy needs to be provided to the DSI which may be problematic for remote, self-sustaining systems that rely on solar power or battery power. Generally, sophisticated calculations or data analysis tends to be better suited for implementation in the cloud. In addition, a cloud based service is well suited to calculating and communicating alarms derived from the inspection results through media such as text messaging or email.

Power

Figure 3A:
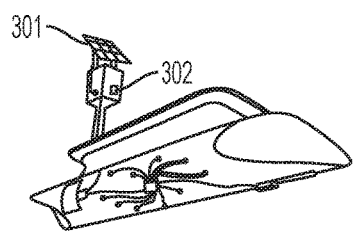
FIGS. 3a-3d show various applications for the system of FIG. 1.

Power may be provided to the system in different ways. For example, in one embodiment, power is provided by the mobile unit which is interconnected to the system through the user interface. In another embodiment, the user interface comprises a battery for powering the system (see, e.g., FIG. 6 and associated text). In such an embodiment, it may be preferable to provide a means of recharging the battery. For example, the user interface may be connected to a solar panel 301 to use solar power to maintain a charge in a battery as shown in FIG. 3a. Alternatively, power may be provided via wind power or other known energy harvesting approach. In yet another embodiment, power is supplied to the system through permanent electrical connection. Such an embodiment may be preferable in situations in which the structure is located near a power source such as in a refinery, power plant or oil platform. Still other means of supplying the system with power will be obvious to one of skill in the art in light of this disclosure.

Operation

Figure 3C:
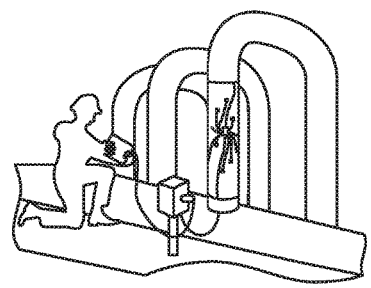
Figure 3B:
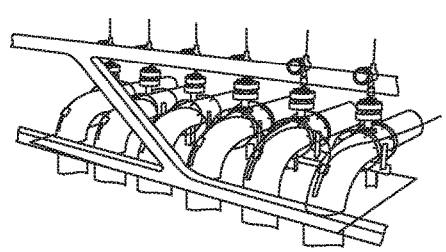
Figure 3D:
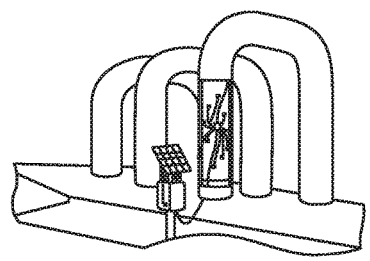

Although the system of FIG. 1 pertains to manual system for monitoring wall thickness of an underground pipe, it should be understood that other embodiments are possible. For example, referring to FIG. 3a-d, different applications of the system are shown. Specifically, in FIG. 3a, the system has a permanently-installed controller for wireless, real time monitoring of a buried pipe. Such a system may include a solar panel 301 as described above. In FIG. 3b, the system is implemented on offshore oil platforms. As shown in FIG. 3c, the system may be implemented in refinery, chemical or power plants. In FIG. 3d, an embodiment similar to that shown in FIG. 3c but for a permanently-installed controller. Furthermore, in FIG. 5, a shear wave sensor is shown for interrogating a certain portion of a weld/crack rather than for determining thickness. Still other applications of the present invention will be obvious to one of skill in light of this disclosure.

Furthermore, while the features described thus far have involved each transducer transmitting a single signal to evaluate the health of an asset (e.g., a thickness transducer measuring the part thickness beneath the transducer or a shear wave transducer interrogating a certain portion of a weld), the system of the present invention is not limited to these applications. In particular, because the DSI is near the sensors and thus can perform computations on the analog sensor signals before they become distorted, the DSI may be configured to execute relatively complex signal processing to provide for a host of different outputs and monitoring options, including, for example, ultrasonic imaging techniques such as ultrasonic phased array/delay and sum beam forming and full matrix capture (FMC)/total focusing method [TFM]

Ultrasonic imaging techniques involve the generation of an ultrasonic image based upon many sound beams impinging upon an area of interest in the asset/structure. It is well known to those skilled in the art to use ultrasonic imaging to inspect for and size defects in welds. Specifically, ultrasonic images are beneficial for a number of reasons including, for example, the increased volume of the portion of the asset that is interrogated and the additional information that can be gleaned through visual or automated interpretation of the image. From an installed monitoring perspective, the formation of weld images to monitor crack growth is particularly advantageous.

Typically, a transducer is moved along the part using robotic manipulation, with "shots" being taken at predetermined intervals. The resulting A-scans are converted into images such as B-Scan and C-Scan types, which are known to those skilled in the art. However, as applied to installed sensors, the use of mechanical manipulation to move the sensor is impractical.

To generate an image using a transducer that is permanently positioned requires the use of phased array techniques in which a transducer is subdivided into many small elements that are each addressed independently from an electrical standpoint. Beam focusing and steering can then be accomplished by controlling the sequence of firing the elements through applied time delays to the ultrasonic transmissions/receptions, and summing the A-scans from all elements together. This method is known to those skilled in the art, and is generically referred to as ultrasonic phased array and "delay and sum beam forming," which is discussed, for example, in "Diagnostic Ultrasound Imaging: Inside Out", $2^{nd}$ edition, Thomas Szabo, Academic Press; 2 edition (Dec. 26, 2013), hereby incorporated by reference.

Figure 7:
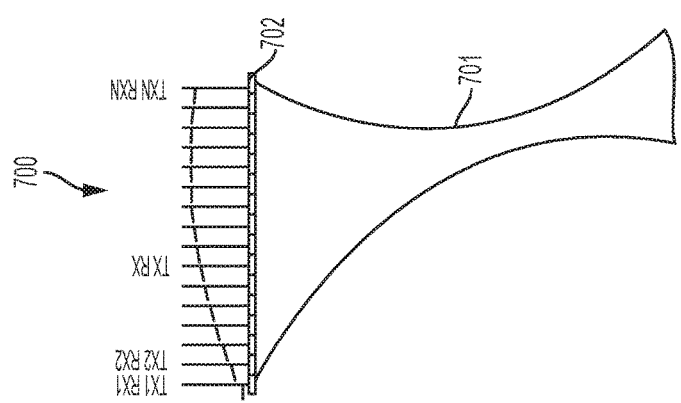
FIG. 7 shows a schematic of a traditional phased array generating a steered focused beam.

Referring to FIG. 7, a schematic view 700 of delay and sum beam forming is shown. Specifically, by applying a time delay sequence to the ultrasonic transmissions/receptions, a single-focused shaped beam 701 can be formed using a conventional phased array of sensor 702. In this manner, a beam can be steered through the volume of an object to facilitate ultrasonic imaging.

While the proposed use of phased array does allow an ultrasonic image to be made with a permanently installed transducer, it is still typically impractical because the phased array technique requires many parallel system channels and onboard processing which requires excessive cost and power. While it is conceivable that any phased array instrument could be used in a permanently installed fashion, the cost and battery life of such a system makes such a system impractical—at this time. Furthermore, the equipment may not be suitable for installation in the hostile environments adjacent to a transducer location and thus may require long umbilical cables between the probe and instrumentation. This is a common issue when performing phased array inspections inside of nuclear power plant containment. The long umbilical cables severely degrade test performance.

As mentioned above, the present invention is not faced with the problem of signal degradation over long cable length because the DSI is proximate to the permanently installed phased array sensors, and, thus, can perform the computations prior to the sensor signals becoming distorted. Specifically, in one embodiment, the DSI is configured to support single transmit and receive channels, and to use a switch matrix to allow the connection of the transmitter and receiver to any combination of system channels. For example, a DSI with a switch matrix sufficient to connect to 16 transducer elements can be arbitrarily configured with, for instance, the TX channel connected to element 1 and the RX channel connected to Channel 16. This allows the DSI to facilitate the known techniques of full matrix capture (FMC) and total focusing method [TFM], which are described, for example, in C. Holmes, B. Drinkwater, and P. Wilcox, "Post-processing of the full matrix of ultrasonic transmit-receive array data for non-destructive evaluation," NDT & E International, vol. 38, no. 8, pp. 701-711, December 2005, hereby incorporated by reference. In this approach, the DSI has only a single transmit and receive channel, and, therefore, can be designed to be very low power. Further, in one embodiment, the TFM operation is performed in post processing on a PC therefore the DSI is only required to collect and transmit data placing no additional computational burden on the DSI.

Figure 9:
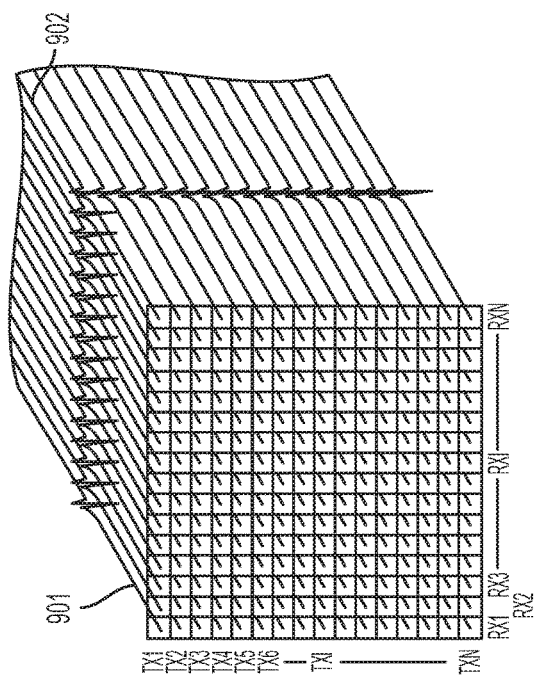
FIG. 9 shows an example of a matrix of data generated using the sensor of FIG. 8.
Figure 8:
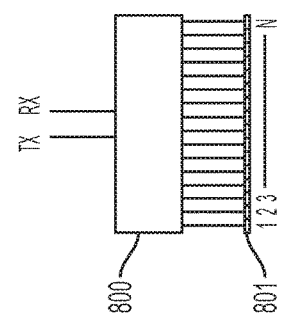
FIG. 8 shows a schematic of one embodiment of a multi-element sensor configured for full matrix capture.

The concept of full matrix capture is described by FIG. 8. A transducer 800 having N elements 801 is shown, where the transmitter (TX) is connected to transducer element j and the receiver is connected to transducer element i. A waveform is collected for each combination of i=1 to N and j=1 to N, creating a matrix of data 901 as shown in FIG. 9. Thus, for an N element transducer, N squared A-scans 902 are collected. These A-scans 902 are transmitted from the DSI to a data collection device such as a tablet PC, industrial PC or to cloud storage as mentioned above.

Figure 10:
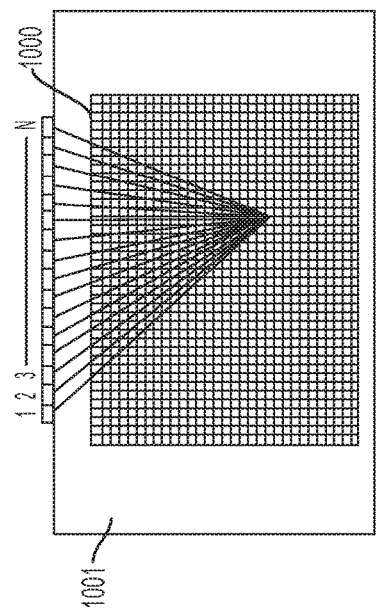
FIG. 10 shows an example of a reconstruction grid based on the matrix of data of FIG. 9.

The second process in the image formation is called the total focusing method (TFM) and, in one embodiment, is performed outside the DSI, for example, on the data collection device, in the cloud or with the user's PC. Specifically, in one embodiment, the steps of applying TFM comprise: (1) defining a computation zone 1001 within the asset/structure. (2) Within that computation zone, defining a reconstruction grid 1000 with defined shape and spacing as shown in FIG. 10. For example, a rectilinear grid with 1 mm×1 mm spacing. (3) At each grid point, computing a time delay for each combination of transmit and receive element, so for an N element array, NA2 time delays are defined. (4) The data point in each A-scan that corresponds to the calculated time in step 3 is collected and summed. This process is repeated for all points of the reconstruction grid. (5) Optionally, a process known as scan conversion can be applied to resample the data points from the reconstruction grid to an image grid, for instance to match screen resolution. (6) A pseudo-color image may then be created by applying a map of colors based upon the amplitude of the data points in the image grid (or reconstruction grid). (7) Pseudo-A scans can also be generated by "slicing" the reconstructed data in a single dimension. Additional operations such as upsampling, gating, threshold detection, and zero crossing measurements can be applied to the A-scan as are known to those skilled in the art. Therefore, in this way, the system of the present invention can be configured to provide ultrasonic images of asset portions of interest rather than simple measurement data.

The system of the present invention can also be configured to provide sophisticated trending information because of the accuracy in the repeatability of the measurements taken. As mentioned above, because the present invention employs permanently installed sensors and stores contextual data, it essentially eliminates variations in repeated measurements. This facilitates sophisticated monitoring for trends. This coupled with the ability of cloud-based data analysis to provide constant and sophisticated analysis of the data obtained, leads to more advanced alarm logic. For example, in thickness gauging, basic alarming might include performing an action such as sending a text message to an interested party when the thickness of a TML falls below a prescribed minimum. This would be described by the following logical expression:

if ($t$<$t$min==true) send alarm

Basic alarms that are common might also include multiple levels of alarming such as t<twarning to flag a TML that has reduced to a point that an operator might want to watch the point but that is not at an absolute minimum value. Corrosion rates might also be alarmed such as an instance where the rate is greater than 10 mils per year.

While these alarms are useful, there is additional capability to be had through the inclusion of more logical expressions. This is accomplished by adding the following operators to the software such as the following: Not, And, Or, Equivalent and NEquivalent. For example, an expression could be constructed as follows:

if ($t$<twarning).and.(rate>10) send alarm.

Many other expressions will be obvious to those of skill in the art in light of this disclosure.

Having thus described a few particular embodiments of the invention, various alterations, modifications, and improvements will readily occur to those skilled in the art. Such alterations, modifications, and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. An ultrasound sensing system for monitoring the condition or integrity of a structure, comprising:

one or more ultrasound sensors being mounted permanently or semi permanently to said structure, each sensor being configured to receive at least one first electrical signal, transmit an ultrasound signal in response to said first electrical signal, receive at least one reflected ultrasound signal, and transmit a second electrical signal in response to said reflected ultrasound signal, said first and second-electrical signals being analog; and at least one digital sensor interface (PS 1) being mounted permanently or semi permanently to said structure to which at least a portion of said sensors are connectable, said DSI being configured to transmit said first electrical signal and receive said second electrical signal, and to generate an A-scan signal based on said first and second electrical signals for each sensor, said DSI being configured to calculate thickness data based on said A-scan signal and having circuitry for transmitting a digital signal and an address corresponding to said at least one DSI.

2. The system of claim 1, wherein at least some of said sensors are dual element sensors.

3. The system of claim 1, wherein said at least one DSI is configured to periodically transit said first electrical signal, generate an A-scan signal, and store said thickness data, and to transmit said digital signal at a subsequent, predetermined time.

4. The system of claim 1, wherein said at least one DSI is configured to transmit said first electrical signal in response to a polling request signal from a controller connected digitally to said DSI.

5. The system of claim 1 were the DSI and said one or more sensors are configured to limit the energy available for the ignition of flammable gas or dust mixtures such that said system can be certified for operation in a hazardous environment as required by ATEX, iECX, NFPA or other such standards and/or certification schemes.

6. The system of claim 1, wherein said DSI contains circuitry and software to interface to temperature monitoring devices, where at least one temperature monitoring device is mounted on the object under test.

7. The system of claim 6, wherein the number of said temperature monitoring devices equals the number of said one or more sensors.

8. The system of claim 6, wherein each temperature monitoring devices is connected to one or more of ultrasonic sensors.

9. The system of claim 1, further comprising:
a digital bus configured to receive said digital signal from said at least one DSI; and
a user interface connected to said bus to receive said digital signal.

10. The system of claim 9, wherein said digital bus is a multi-drop bus.

11. The system of claim 9, wherein said user interface comprises a connector to interconnect a controller.

12. The system of claim 11, wherein said controller is a tablet.

13. The system of claim 9, wherein said user interface comprises a permanently-installed wireless controller for transmitting a wireless signal based on said digital signal.

14. The system of claim 13, wherein said wireless controller is solar powered.

15. The system of claim 9, wherein at least one DSI comprises multiple DSIs each connected to said digital bus.

16. The system of claim 1, wherein at least one of said one or more sensors is a multi-element sensor and said DSI is configured to execute full matrix capture on data obtained from said multi-element sensor.

17. The system of claim 16, further comprising a computational device, discrete from said DSI, configured to use a total focusing method on said data of said full matrix capture to generate an ultrasonic image.

18. The system of claim 17, wherein said computational device is a remote, distributed computational resource.

19. The system of claim 17 wherein said computational device is configured to use a total focusing method on said data of said full matrix capture to determine the thickness of an asset.

20. The system of claim 1, wherein said DSI is configured to transmit said digital signal wirelessly.

21. The system of claim 1, wherein said one or more sensors comprises a plurality of sensors and wherein said plurality of sensors is connected to a single DSI.

22. The system of claim 1, wherein said digital signal does not comprise said A-scan signal.

23. The system of claim 1, wherein said digital signal comprises location data for said DSI.

24. A digital sensor interface (DSI) for use in an ultrasound sensing system for monitoring the condition or integrity of a structure, said DSI comprising:

- transmit and receive circuitry to which at least one or more sensors are operatively connectable, said transmit and receive circuitry being configured to transmit a first electrical signal to each of said sensors and to receive a second electrical signal from said each of said sensors responsive to said first electrical signal;
- a digital processor being configured to calculate an A-scan signal based on said first and second signals, and to calculate thickness data based on said A-scan signal; and
- a digital transceiver to transmit a digital signal comprising at least said thickness data.

25. The DSI of claim 24, wherein said digital transceiver is configured to transmit said digital signal wirelessly.

26. The DSI of claim 24, wherein said digital transceiver is configured to transmit said digital signal over a digital bus.

27. The DSI of claim 24, wherein said first and second signals are analog and said DSI further comprises a digital converter to digitize data related to said first and second signals.

28. The DSI of claim 24, wherein said digital signal does not comprise said A-scan signal.

29. The DSI of claim 24, wherein said digital signal comprises location data for said DSI.

* * * * *